United States Patent

Shesol

[19]

[11] Patent Number: 5,918,599
[45] Date of Patent: Jul. 6, 1999

[54] TRACHEOSTOMY TUBE DRESSING AND SUPPORT DEVICE

[75] Inventor: Barry F. Shesol, Aurora, Colo.

[73] Assignee: Tapeless Technologies, Inc., Aurora, Colo.

[21] Appl. No.: 08/914,635

[22] Filed: Aug. 19, 1997

[51] Int. Cl.[6] .................................................. A61M 16/00
[52] U.S. Cl. ............................... 128/207.17; 128/DIG. 26
[58] Field of Search ........................ 128/207.17, 207.29, 128/DIG. 26, 207.14, 200.26

[56] References Cited

U.S. PATENT DOCUMENTS

| | | | |
|---|---|---|---|
| 3,160,158 | 12/1964 | Rayhart ............................ | 128/DIG. 26 |
| 3,286,713 | 11/1966 | Kurtz et al. ........................ | 128/207.14 |
| 3,422,817 | 1/1969 | Mishkin et al. ................. | 128/DIG. 26 |
| 3,683,911 | 8/1972 | McCormick .................... | 128/DIG. 26 |
| 4,221,215 | 9/1980 | Mandelbaum .................. | 128/DIG. 26 |
| 5,000,741 | 3/1991 | Kalt .................................... | 128/207.17 |
| 5,357,952 | 10/1994 | Schuster et al. ................. | 128/DIG. 26 |
| 5,551,421 | 9/1996 | Noureldin et al. .............. | 128/DIG. 26 |

*Primary Examiner*—Aaron J. Lewis
*Attorney, Agent, or Firm*—Edwin H. Crabtree; Ramon L. Pizarro; Donald W. Margolis

[57] ABSTRACT

A tracheostomy tube dressing and support device unit used for holding a tracheostomy tube in place and holding a primary wound dressing, such as a sterile gauze pad, next to a tube insertion site in the front of a patient's neck. The unit includes an elastic bi-directional wrap stretchable in opposite directions along a length of the wrap. One end of the wrap includes hook fasteners for engaging an opposite end of the wrap and holding it in place around the neck. The wrap includes a window opening with a pair of hook fastener strips attached to opposite sides of the window opening and on an outside of the wrap. The hook fastener strips are used for releasable receipt through flange openings in opposite sides of a tracheostomy tube flange. When the hook fastener strips are threaded through the flange openings, the strips are secured to loop fastener landing pads thus holding the tracheostomy tube firmly in place. Attached to an inside of the wrap are a plurality of hook fasteners on opposite side of the window opening for holding the wound dressing. The wound dressing is adapted for receipt around and next to a portion of the tracheostomy tube and the tube insertion site.

12 Claims, 1 Drawing Sheet

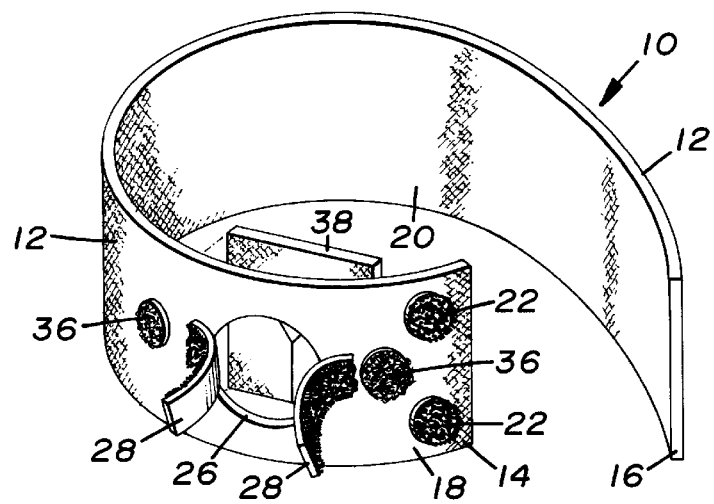
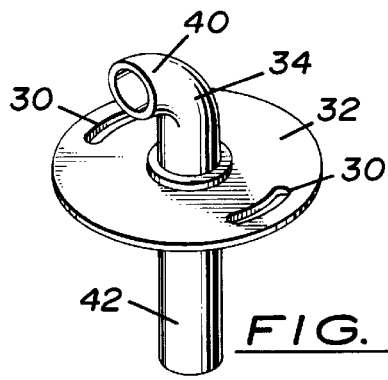
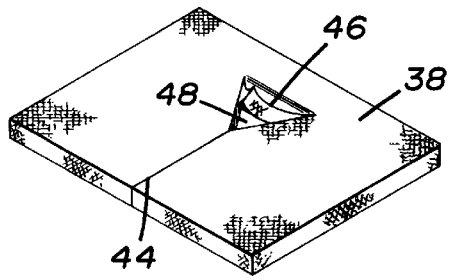
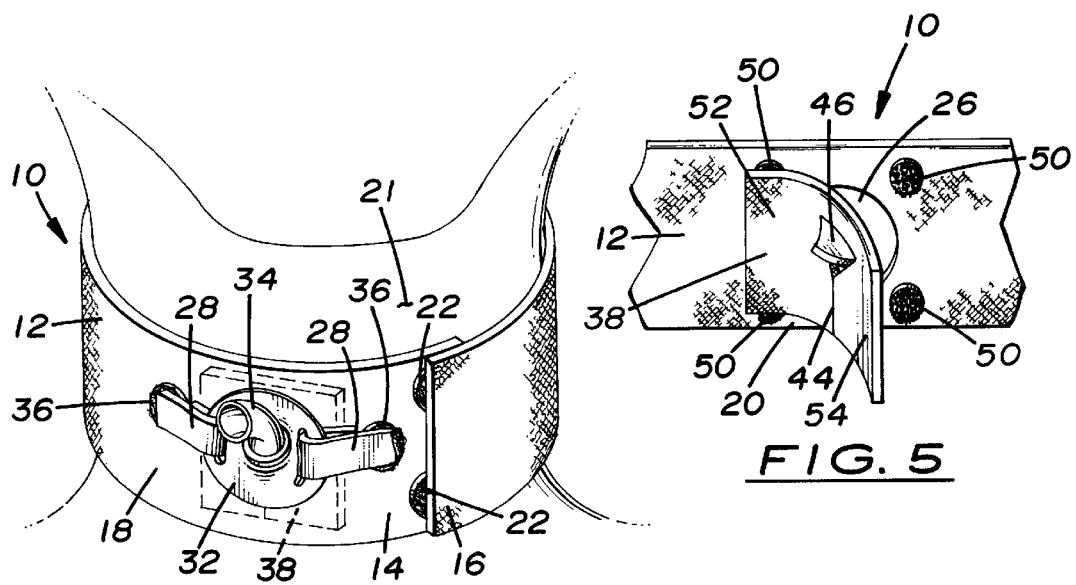

TRACHEOSTOMY TUBE DRESSING AND SUPPORT DEVICE

BACKGROUND OF THE INVENTION (a). Field of the Invention

This invention relates to the holding of tracheostomy tubes and like medical devices and more particularly, but not by way of limitation, to a tracheostomy tube dressing and support unit.

(b). Discussion of Prior Art

The two concerns of a healthcare provider with reference to a tracheostomy tube and like medical tubes are 1. secure anchorage of the tube and 2. maintenance of the insertion site wound in the neck. To date, these two needs have been addressed by separate devices. This invention relates to a one piece unit which provides for both medical concerns.

At present, the tracheostomy tube is held in place by one of two concepts. The first is narrow, shoe-lace like cotton tape which wraps around the neck and ties to opposite sides of the tracheostomy tube flange. This technique has failings related to:

1. Danger of constriction of the airway or the blood supply to head by the rope-like tape.
2. Irritation to the neck by the rubbing of the narrow band of material which worsens as the duration of the usage lengthens. In addition, as the tape becomes encrusted with secretions and drainage from around the tube, the tape looses it's softness and flexibility.
3. The securing knots may come undone which lead to the danger of the life saving tracheostomy tube becoming dislodged and the airway lost.
4. Difficult to adjust for comfort since there is a fine line of comfort vs. proper constriction for a secure application of the tube. Each time the tape must be untied, rethreaded and retied.

A second technique involves the use of velcro straps which slip through the opposite sides of the tube flange, but which are part of a minimally flexible, non-washable, non reusable band. This band for supporting tracheostomy tubes in described in U.S. Pat. No. 4,331,144 to Wapner.

Neither of the above mentioned techniques provide for attention to the second need by the heathcare provider, i.e., the maintenance of the wound at the insertion site.

In U.S. Pat. No. 5,456,660 issued to the subject inventor and Dr. Marshall Reich, a wound dressing support device is described for holding a variety of standard dressings in place on top of an open wound. The support device includes an elongated elastic unidirectional wrap with a window opening therein. This support device does not address the holding of a tracheostomy tube in place and the maintenance of the tube insertion site.

U.S. Pat. No. 4,732,146 to Fasline et al. discloses a surgical wound dressing device having a frame with an opening for receiving different types of wound dressings. A dressing is held in place by straps attached to one side of the frame with one end of the straps including releasable Velcro fasteners.

U.S. Pat. No. 4,917,112 to Kalt describes a bandage having an opening with the opening covered with a transparent membrane. The membrane is designed to allow air and vapors to permeate outward from the wound and prevent contaminants from entering in the opposite direction.

In U.S. Pat. No. 4,909,243 to Frank et al., a two piece wound dressing is shown having an adhesive layer on one side of a baseplate with an opening in the baseplate to expose the wound and the epithelium area around the wound. A second adhesive layer on one side of a wound pad secures a wound dressing above the opening in the baseplate.

U.S. Pat. No. 4,907,579 to Kum, U.S, Pat. No. 5,167,613 to Karami et al., and U.S. Pat. No. 3,779,242 to McCullough disclosed different types of adhesive bandages for providing open areas to wounds to enhance healing. In U.S. Pat. No. 5,036,838 to Sherman, a foam plastic orthopedic fabric is described having a Velcro tab at one end of the fabric.

In U.S. Pat. No. 4,470,410 to Elliott a stretchable sleeve is shown with Velcro fasteners at the ends of the sleeve. The sleeve includes a central opening with a releasable flap for retaining an intravenous tube or the like.

U.S. Pat. Nos. 4,709,695 to Kohn et al., 4,399,816 to Spangler, 5,086,763 to Hathman, and 4,926,883 to Strock all describe different types of wound surrounding dressings and bandages. Also U.S. Pat. Nos. 4,190,054 to Brennan and 4,658,811 to Beaird disclose stretchable bandages having loop and hook type attachment ends for encircling the head of a patient.

None of the above mentioned prior art patents disclose the unique structure and advantages of the subject invention as described herein when addressing the need of a tracheostomy tube dressing and support device for holding a tube in place and at the same time holding a primary dressing next to the tube insertion site.

SUMMARY OF THE INVENTION

In view of the foregoing, it is a primary object of the subject invention to secure a tracheostomy tube in a safe, adjustable reusable fashion, and at the same time provide for a mechanism to hold and secure primary wound dressings which find their application around or over the tracheostomy tube. The various functions of this device are accomplished by the unique combination of 1. material 2. design for ease 3. design for safety and 4. combination of purpose with anatomical considerations.

Another object of the invention is the advantage of using a non-latex washable, reusable, bi-directional material which can be cut and customized for anatomical considerations to the patient, such as neck size, other wounds, neck flexibility and tracheostomy tube size. As the material is cut, it does not fray or unravel. The stretch of the material is an improvement over the relatively stiff commercially available devices now in use. The safety factor attributable to this stretch is significant, because it will quickly and automatically, by it's nature of construction, allow for unexpected or expected swelling with an increase in the girth of the neck, without compromising blood flow to the head and brain.

Still another object of the invention is the material used is non-allergic, washable and reusable. The present commercially available unit is not washable and cannot be used for more than 48 hours per the instructions on the unit's packaging.

Yet another object of the unique tracheostomy tube holder are the following design features and their advantages.

a. A side (of the neck) opening and closure point by means of a hook fastener set of tabs which attach anywhere to the material itself. Excess material can be cut off for "custom sizing".

b. The width of the material wrap which encircles the neck is wide enough (2¾ to 6 inches) to give a comfortable application without any rolling of the edges from excess width.

c. A window opening to allow the tracheostomy tube and flange to adequately, but yet securely slip through.

d. At each side of the window opening, ½ inches from the window edge, is attached a hook fastener strap, 2½×⅜ inches, sewn hook side up, which points toward the window opening. Each strap is then threaded through openings in the opposite sides of the tube's flange. The strap then is folded back over itself to securely and firmly attach to a loop fastener landing pad, ½ inches circular, at a distance of 1½ inches from the edge of the window opening on it's respective side. This permits quick, easy, firm and adjustable anchoring of the tracheostomy tube itself.

e. The subject support device includes hook fastener tabs to be attached by adhesive or permanently attached to an underside of the wrap and next to opposite sides of the window opening. These hook fastener tabs will then secure around the tube itself any primary wound dressing that the health care provider may choose to use to manage the tracheostomy wound.

In summation, the invention provides one complete unit including:

a. A means to secure a tracheostomy tube which is 1. washable 2. reusable 3. hypoallergic 4. adjustable 5. bi-directional 6. customizable 7. incomparably safe.

b. Able to secure and maintain any primary wound dressing simultaneously to the tracheostomy tube wound.

The subject tracheostomy tube dressing and support unit includes an elastic bi-directional wrap which is stretchable in opposite directions along a length of the wrap. One end of the wrap includes hook fasteners for engaging an opposite end of the wrap and holding it in place around a patient's neck. The wrap includes a window opening with a pair of hook fastener strips attached to opposite side of the opening and on the outside of the wraps The hook fastener strips are used for releasable receipt through flange openings in opposite sides of an annular tracheostony tube flange. The flange is part of the tracheostomy tube. When the hook fastener strips are threaded through the flange openings, the strips are bent backwards and secured to loop fastener landing pads on opposite sides of the window opening thus holding the tracheostomy tube firmly in place. Attached to an inside of the wrap are a plurality of hook fasteners on opposite side of the window opening for holding a primary wound dressing such as a sterile gauze pad and the like. The wound dressing is adapted for receipt around and next to the tracheostomy tube and the tube insertion site.

These and other objects of the present invention will become apparent to those familiar with medical wound dressings and problems related to holding a tracheostomy tube in place adjacent a neck entry site outlined in the following detailed description, showing novel construction, combination, and elements as described, and particularly defined by the claims, it being understood that changes in the precise embodiments to the disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view of the tracheostony tube dressing and support device made of a bi-directional wrap and a window opening therein. On opposite sides of the window opening are a pair of hook fastener strips used for releasable engagement of an annular flange disposed around a tracheostomy tube. Also shown in this drawing is a primary wound dressing such as a sterile gauze pad positioned for attachment to the inside of opposite sides of the window opening in the wrap.

FIG. 2 is a perspective view of standard tracheostomy tube with tube inlet and tube outlet. Disposed around the tube is an annular tube flange with a pair of openings in opposite sides of the flange.

FIG. 3 is a perspective view of a standard primary wound dressing. In this example, the dressing is a 4 inch by 4 inch sterile gauze pad. The pad includes a "Y" shaped cut therein for receipt around a portion of the tracheostomy tube.

FIG. 4 is a perspective view of the subject invention secured around a patient's neck with the wrap and hook fastener strips holding the tracheostomy tube in place and the sterile gauze pad held in place next to the inside of the wrap and around a portion of the tracheostomy tube.

FIG. 5 is a perspective view of a portion of the inside of the bi-directional wrap with window opening. The gauze pad is shown releasably attached to a pair of hook fasteners on one side of the window opening in the wrap.

DESCRIPTION OF THE PREFERRED EMBODIMENTS

In FIG. 1, a perspective view of the tracheostomy tube dressing and support device unit is shown and having general reference numeral 10. The unit 10 includes a bi-directional wrap 12 made of loose weave material and stretchable along a length of the wrap in opposite directions. The wrap 12 includes a first end 14, a second end 16, an outside 18 and an inside 20 which is placed next to the skin of a patient's neck 21 as shown in FIG. 4. The first end 14 of the wrap 12 includes a pair of wrap hook fasteners 22 which are used to engage the loose weave material on the inside 20 of the second 16. The second end 16 of the wrap 12 may be cut to length for different sizes of necks and customizing the unit 10. Also, the wrap hook fasteners 22 have infinite adjustments along the length of the second end 16 of the wrap 12 for a comfortable fit around the patient's neck 21.

The wrap 12 is characterized by having a window opening 26 therethrough. The window opening 26 may have various geometric configurations and in the drawings is shown having an annular shape. The window opening 26 has typical dimensions in a range of 2¼ inches in length and 1¼ inches width. While these dimensions are mentioned, it can be appreciated that they may vary and be greater or smaller without departing from the spirit and scope of the invention. Adjacent opposite sides of the window opening 26 is a pair of hook fastener strips 28 which are used for receipt through a pair of flange openings 30 in a flange 32. The flange 32 is disposed around a tracheostomy tube 34. The tracheostomy tube 34 is shown in FIG. 2. One end of the hook fastener strips 28 is secured to the wrap 10 with the other end of the strips 28 releasably attached to a pair of loop fastener landing pads 36. The landing pads 36 are also attached to the outside 18 of the wrap 12 and on opposite sides of the window opening 26. Also shown in this drawing is a primary wound dressing such as a sterile gauze pad 38 which is positioned for attachment on the inside 20 of the wrap 12 and disposed over the window opening 26. The gauze pad 38 is shown in greater detail in FIG. 3.

In FIG. 2, a standard tracheostomy tube 34 is shown having a first tube end 40 and a second tube end 42. The second tube end 42 is received through a tube insertion site in a patient's neck. The insertion site is not shown in the drawings. Also shown in these drawings is the flange 32 disposed around the tube 34. The flange 32 includes the flange openings 30 which are used for holding the tracheostomy tube 34 in place.

In FIG. 3, a perspective view of a typical standard primary wound dressing is shown. In this example, the dressing is a 4 inch by 4 inch sterile gauze pad 38. The wound dressing may vary in size and shape and as mentioned above the 4×4 pad 38 is used as an example only. The pad 38 includes a "Y" shaped cut 44 with an upper portion of the cut 44 forming a tab 46 which is folded back to form an opening 48 for receiving a portion of the second tube end 42 of the tracheostomy tube 34 therearound. The gauze pad 38 is received around the skin of the tube insertion site for absorbing any drainage during the use of the tracheostomy tube 34.

In FIG. 4, a perspective view of the subject invention is shown secured around the patient's neck 21 with the wrap 12 and hook fastener strips 28 holding the tracheostomy tube 34 in place. The sterile gauze pad 38 is also shown in dotted lines and held in place next to the inside 20 of the wrap 12 and around a portion of the second end 42 of the tracheostomy tube 32. In this view, the first end 14 of the wrap 12 is shown attached to the second end 16 of the wrap 12 using the hook fasteners 22. The hook fastener strips 28 are shown received through the flange openings 30 and releasably secured to the loop fastener landing pads 36.

In FIG. 5, a perspective view of a portion of the inside 20 of the bi-directional wrap 12 with window opening 26 is shown. The gauze pad 38 with "Y" shaped cut 44 and tab 46 are also shown. A first side 52 of the gauze pad 38 is shown releasably attached to a pair of dressing hook fasteners 50 on one side of the window opening in the wrap 24. A second side 54 of the gauze pad 38 is shown in position for releasable attachment to another pair of dressing hook fasteners 50 on the other side of the window opening 26. By the nature of the loose weave making up a sterile gauze pad, the hook fasteners 50 are readily adaptable for engaging and releasing the loose weave of the pad 38. The gauze pad 38 and drainage thereon can be monitored for changing by quickly releasing the first end 14 of the wrap 12 from the second end 16 and folding the first end 14 backwards and viewing the gauze pad 38.

While the invention has been particularly shown, described and illustrated in detail with reference to the preferred embodiments and modifications thereof, it should be understood by those skilled in the art that changes in form and detail may be made therein without departing from spirit and scope of the invention as claimed, except as precluded by the prior art.

The embodiments of the invention for which an exclusive privilege and property right is claimed are defined as follows:

1. A tracheostomy tube dressing and support device unit, the unit used for holding a tracheostomy tube in place on a patient's neck, a tracheostomy tube having a flange therearound with a pair of flange openings on opposite side of a flange, the unit comprising:

a wrap, one end of said wrap having wrap fastener means for engaging an opposite end of said wrap and holding said wrap in place around a patient's neck, said wrap having an inside and an outside;

a window opening in said wrap;

tube fastener means attached to opposite sides of said window opening and on the outside of said wrap, said tube fastener means adapted for releasable receipt through flange openings in a flange of a tracheostomy tube and releasably engaging a portion of said wrap disposed on opposite sides of said window opening.

2. The device as described in claim 1 further including a primary wound dressing, said primary wound dressing secured to the inside of said wrap.

3. The device as described in claim 2 wherein said primary wound dressing has a "Y" shaped cut therein, said "Y" shaped cut adapted for receipt around a portion of a tracheostomy tube.

4. The device as described in claim 2 wherein said wrap includes primary wound dressing fastening means disposed on opposite sides of said window opening and on the inside of said wrap, said primary wound dressing fastening means for releasable attachment to said primary wound dressing.

5. A tracheostomy tube dressing and support device unit, the unit used for holding a tracheostomy tube in place and holding a primary wound dressing next to a tube insertion site in the front of a patient's neck, a tracheostomy tube having a flange therearound with a pair of flange openings on opposite side of a flange, the unit comprising:

a wrap, one end of said wrap having wrap hook fasteners for engaging an opposite end of said wrap and adapted for holding said wrap in place around a patient's neck, said wrap having an inside and an outside;

a window opening in said wrap;

tube fastener means disposed on opposite sides of said window opening, said tube fastener means for releasable receipt through flange openings in a flange of a tracheostomy tube and releasably engaging a portion of said wrap on opposite sides of said window opening; and wound dressing attachment means disposed on opposite sides of said window opening and on the inside of said wrap, said wound dressing attachment means adapted for releasably holding the primary wound dressing.

6. The unit as described in claim 5 wherein said wrap is an elastic bi-directional wrap stretchable in opposite directions along a length of said wrap.

7. The unit as described in claim 5 wherein said tube fastener means is a pair of hook fastener strips, one end of said hook fastener strips attached to opposite sides of said window opening and on the outside of said wrap.

8. The unit as described in claim 7 wherein an opposite end of said hook fastener strips are attached to said wrap by releasably engaging a pair of loop fastener landing pads disposed on opposite sides of said window opening.

9. The unit as described in claim 5 wherein said wound dressing attachment means is plurality of dressing hook fasteners disposed on opposite sides of said window opening and on the inside of said wrap, said hook fasteners adapted for releasably holding the primary wound dressing on said wrap.

10. A tracheostomy tube dressing and support device unit, the unit used for holding a tracheostomy tube in place and holding a primary wound dressing next to a tube insertion site in the front of a patient's neck, a tracheostomy tube having a flange therearound with a pair of flange openings on opposite side of a flange, the unit comprising:

a wrap, one end of said wrap having wrap hook fasteners for engaging an opposite end of said wrap and adapted for holding said wrap in place around a patient's neck, said wrap having an inside and an outside;

a window opening in said wrap;

a pair of hook fastener strips having one end attached to opposite sides of said window opening and on an outside of said wrap, an opposite end of said hook fastener strips adapted for releasable receipt through flange openings in a flange of a tracheostomy tube and engaging a pair of loop fastener landing pads disposed on opposite sides of said window opening; and a plurality of dressing hook fasteners disposed on opposite sides of said window opening and on the inside of said wrap, said dressing hook fasteners adapted for releasably holding the primary wound dressing.

11. The unit as described in claim 10 wherein said wrap is an elastic bi-directional wrap stretchable in opposite directions along a length of said wrap.

12. The unit as described in claim 11 wherein said wrap is made of a loose weave material, said loose weave material releasably engaging said wrap hook fasteners when said wrap is held in place around a patient's neck.

* * * * *